United States Patent
Catalan

(10) Patent No.: US 8,328,782 B2
(45) Date of Patent: Dec. 11, 2012

(54) HYDROPHOBIC SURFACE COATED LIGHT-WEIGHT NONWOVEN LAMINATES FOR USE IN ABSORBENT ARTICLES

(75) Inventor: Kemal Vatansever Catalan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1145 days.

(21) Appl. No.: 11/061,999

(22) Filed: Feb. 18, 2005

(65) Prior Publication Data

US 2006/0189956 A1  Aug. 24, 2006

(51) Int. Cl.
*A61F 13/15* (2006.01)
(52) U.S. Cl. ............. 604/385.04; 381/385.101; 381/378
(58) Field of Classification Search .................. 604/381, 604/385.24–385.29, 385.01, 358, 378, 385.101, 604/385.04
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,848,594 A | 11/1974 | Buell |
| 3,849,241 A | 11/1974 | Butin et al. |
| 3,860,003 A | 1/1975 | Buell |
| 3,911,173 A | 10/1975 | Sprague, Jr. |
| 4,041,203 A | 8/1977 | Brock et al. |
| 4,340,563 A | 7/1982 | Appel et al. |
| 4,381,781 A | 5/1983 | Sciaraffa et al. |
| 4,515,595 A | 5/1985 | Kievit et al. |
| 4,573,986 A | 3/1986 | Minetola et al. |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,710,189 A | 12/1987 | Lash |
| 4,785,996 A | 11/1988 | Ziecker et al. |
| 4,795,454 A | 1/1989 | Dragoo |
| 4,808,178 A | 2/1989 | Aziz et al. |
| 4,834,735 A | 5/1989 | Alemany et al. |
| 4,842,666 A | 6/1989 | Werenicz |
| 4,846,815 A | 7/1989 | Scripps |
| 4,857,067 A | 8/1989 | Wood et al. |

(Continued)

FOREIGN PATENT DOCUMENTS

EP    0331774 A1 *  9/1989

(Continued)

OTHER PUBLICATIONS

Hatch, Kathryn L., Textile Science, 1993, West Publishing, p. 26.*

(Continued)

*Primary Examiner* — Jacqueline F. Stephens
(74) *Attorney, Agent, or Firm* — Abbey A. Lopez; John G. Powell; Eric T. Addington

(57) ABSTRACT

The present invention relates to absorbent articles which include one or more barrier members comprising a light-weight nonwoven laminate that has been treated with a hydrophobic surface coating intended to render such components impermeable to liquids having relatively low surface tensions.

20 Claims, 8 Drawing Sheets

U.S. PATENT DOCUMENTS

| | | | |
|---|---|---|---|
| 4,888,231 A | 12/1989 | Angstadt | |
| 4,889,576 A * | 12/1989 | Suganuma et al. | 156/249 |
| 4,894,060 A | 1/1990 | Nestegard | |
| 4,909,803 A | 3/1990 | Aziz et al. | |
| 4,938,753 A | 7/1990 | Van Gompel et al. | |
| 4,940,464 A | 7/1990 | Van Gompel et al. | |
| 4,946,527 A | 8/1990 | Battrell | |
| 4,988,344 A | 1/1991 | Reising et al. | |
| 4,988,345 A | 1/1991 | Reising | |
| 5,092,861 A | 3/1992 | Nomura et al. | |
| 5,147,345 A | 9/1992 | Young et al. | |
| 5,151,092 A | 9/1992 | Buell et al. | |
| 5,171,391 A * | 12/1992 | Chmielewski et al. | 156/229 |
| 5,221,274 A | 6/1993 | Buell et al. | |
| 5,234,423 A | 8/1993 | Alemany et al. | |
| 5,246,433 A | 9/1993 | Hasse et al. | |
| 5,399,175 A * | 3/1995 | Glaug et al. | 604/385.101 |
| 5,449,553 A * | 9/1995 | Griffith | 428/332 |
| 5,492,751 A * | 2/1996 | Butt et al. | 428/198 |
| 5,569,234 A | 10/1996 | Buell et al. | |
| H1630 H | 1/1997 | Roe et al. | |
| 6,120,487 A | 9/2000 | Ashton | |
| 6,120,489 A | 9/2000 | Johnson et al. | |
| 6,420,627 B1 * | 7/2002 | Ohnishi et al. | 604/384 |
| 6,482,191 B1 | 11/2002 | Roe et al. | |
| 6,506,187 B1 * | 1/2003 | Andersson et al. | 604/385.28 |
| 6,706,946 B1 | 3/2004 | Lankhof et al. | |
| 2002/0142691 A1 * | 10/2002 | Powers et al. | 442/400 |
| 2005/0177123 A1 * | 8/2005 | Catalan | 604/381 |

FOREIGN PATENT DOCUMENTS

| | | | |
|---|---|---|---|
| EP | 0761846 A2 * | 3/1997 | |
| EP | 1155667 A2 | 11/2001 | |
| EP | 0670154 B2 | 4/2004 | |
| JP | 2-088056 A | 3/1990 | |
| JP | 1994-070954 | 3/1994 | |
| JP | 9-170112 | 8/1995 | |
| JP | 2002-088633 | 3/2002 | |
| WO | WO 01/46505 A2 | 6/2001 | |
| WO | WO 2005/005704 A2 | 1/2005 | |

OTHER PUBLICATIONS

Yoshida, Zenji, Fused Core Material, JP Publication 62-212487, Sep. 18, 1987, abstract.*

U.S. Appl. No. 10/824,122, filed Apr. 14, 2004, Gregory Ashton.

U.S. Appl. No. 11/055,743, filed Feb. 10, 2005, Kemal V. Catalan.

* cited by examiner

HYDROPHOBIC SURFACE COATED LIGHT-WEIGHT NONWOVEN LAMINATES FOR USE IN ABSORBENT ARTICLES

FIELD OF THE INVENTION

The present invention relates to absorbent articles including one or more light-weight nonwoven laminates that have been treated with a hydrophobic surface coating intended to render the laminate impermeable to liquids having relatively low surface tensions.

BACKGROUND OF THE INVENTION

Disposable absorbent articles such as diaper, training pants, sanitary napkins, pantiliners, and adult incontinence articles are commonly used to absorb and contain body exudates. Such articles are intended to prevent body exudates from soiling, wetting, or otherwise contaminating clothing or other articles, such as bedding, that may come into contact with the absorbent article. However, absorbent articles are still prone to failure. A common point of failure is when body exudates escape the boundaries of the article as a result of leakage from gaps between the article and the wearer's skin or from seepage through the material that makes up the absorbent article. The latter instance is often caused by the inability of the materials to serve as an effective barrier to such bodily fluids. For example, with sufficient pressure or loading, urine may penetrate through the materials that serve as a barrier, such as a leg cuff. Additionally, loose fecal matter that is not easily absorbed by the absorbent article tends to remain on top of the article's liquid receiving member. During the course of wear, fecal matter may spread over the liquid receiving member and may eventual leak from gaps between the article and the wearer or seep through barrier material.

Contemporary absorbent articles generally have a topsheet, a backsheet, an absorbent core, a barrier cuff, and a gasketing cuff. Other additional features such as barriers, pockets, spacers, transverse barriers, apertured topsheets and the like have been used to isolate, immobilize, or confine body exudates. While many attempts have been made at improving the barrier characteristics of an absorbent article, absorbent article design generally involves a balancing of factors. As a result, improved barrier characteristics are often countered with some undesirable characteristic. For example, an absorbent article can be made virtually liquid impervious through the use of polymeric films, but such films are also generally vapor and air impermeable. Although the article has aggressive barrier properties, the absorbent article may also occlude the skin of the wearer, which may result in diaper rash. The use of nonwoven materials is common in absorbent articles since they provide vapor and air impermeability, but nonwovens are subject to seepage given the appropriate conditions.

One way to improve the liquid retention capability of nonwovens is by increasing the basis weight. Nonwovens with higher basis weights generally have improved liquid impermeability. Another way to improve the liquid retention capability of nonwoven is through the use of nonwoven laminates. Multilayer nonwoven construction using continuous filaments (e.g., spunbond filaments) and fine fibers (e.g., meltblown fibers and nanofibers) is well known in the art. A common multilayer nonwoven construction is a tri-laminate spunbond-meltblown-spunbond (SMS) material. The meltblown layer exhibits liquid impermeability but lacks abrasion resistance and strength. The spunbonded layers are provided to impart needed abrasion resistance and strength to the laminate. While SMS materials provide a degree of liquid impermeability and maintain some vapor permeability, each layer of the SMS material may require a minimum basis weight in order to provide the layer's requisite characteristics. Increased basis weight is generally an undesirable characteristic in disposable absorbent articles. Increased basis weight can result in undesirable stiffness of the material, increased cost of material manufacture, and increased disposal volume.

Accordingly, it would be desirable to provide an absorbent article having a light-weight nonwoven material with improved barrier properties. Furthermore, it would be advantageous to provide an economical disposable article having a light-weight nonwoven material with the ability to minimize the negative effects of feces or other viscous bodily waste on the wearer or the caregiver. It would also be advantageous to provide an article which is designed to chemically or physically interact with materials making up the article and in order to reduce the amount of leakage and/or seepage that may occur.

SUMMARY OF THE INVENTION

In order to help resolve at least some of the problems described above, the present invention provides an article which has a liquid pervious first topsheet having an interior surface and an exterior surface; a backsheet having an interior surface and an exterior surface wherein said backsheet is attached to said topsheet along a periphery; an absorbent core disposed between said topsheet and said backsheet; and a barrier member selected from the group consisting of a core cover, an outer cover, a barrier cuff, a gasketing cuff, a waist feature, an elasticized topsheet, and combinations thereof; wherein said barrier member comprises a light-weight nonwoven laminate. The article may further comprise a hydrophobic surface coating disposed on at least one surface of the light-weight nonwoven laminate wherein said coating comprises one or more silicone polymers and wherein said coating is substantially free of aminosilicones.

The present invention is further directed to an absorbent article comprising a liquid pervious first topsheet having an interior surface and an exterior surface, a backsheet having an interior surface and an exterior surface wherein said backsheet is at least partially joined to said topsheet, an absorbent core disposed between said topsheet and said backsheet, and at least one cuff disposed along an outer edge of the article, said cuff having interior and exterior surfaces. The cuff may comprise a nonwoven laminate treated with a hydrophobic surface coating disposed on at least one surface of said nonwoven laminate wherein said coating comprises one or more silicone polymers and wherein said coating is substantially free of aminosilicones.

The present invention is further directed to a disposable substrate article comprising a nonwoven substrate. The nonwoven substrate comprises a first continuous filaments layer, a second continuous filaments layer, and a fine fiber layer having a basis weight of less than about 1.5 gsm disposed between the first continuous filaments layer and the second continuous filaments layer. A hydrophobic surface coating may be disposed on at least one surface of said substrate, wherein said coating comprises one or more silicone polymers and wherein said coating is substantially free of aminosilicones.

DETAILED DESCRIPTION OF THE INVENTION

Figure 1:
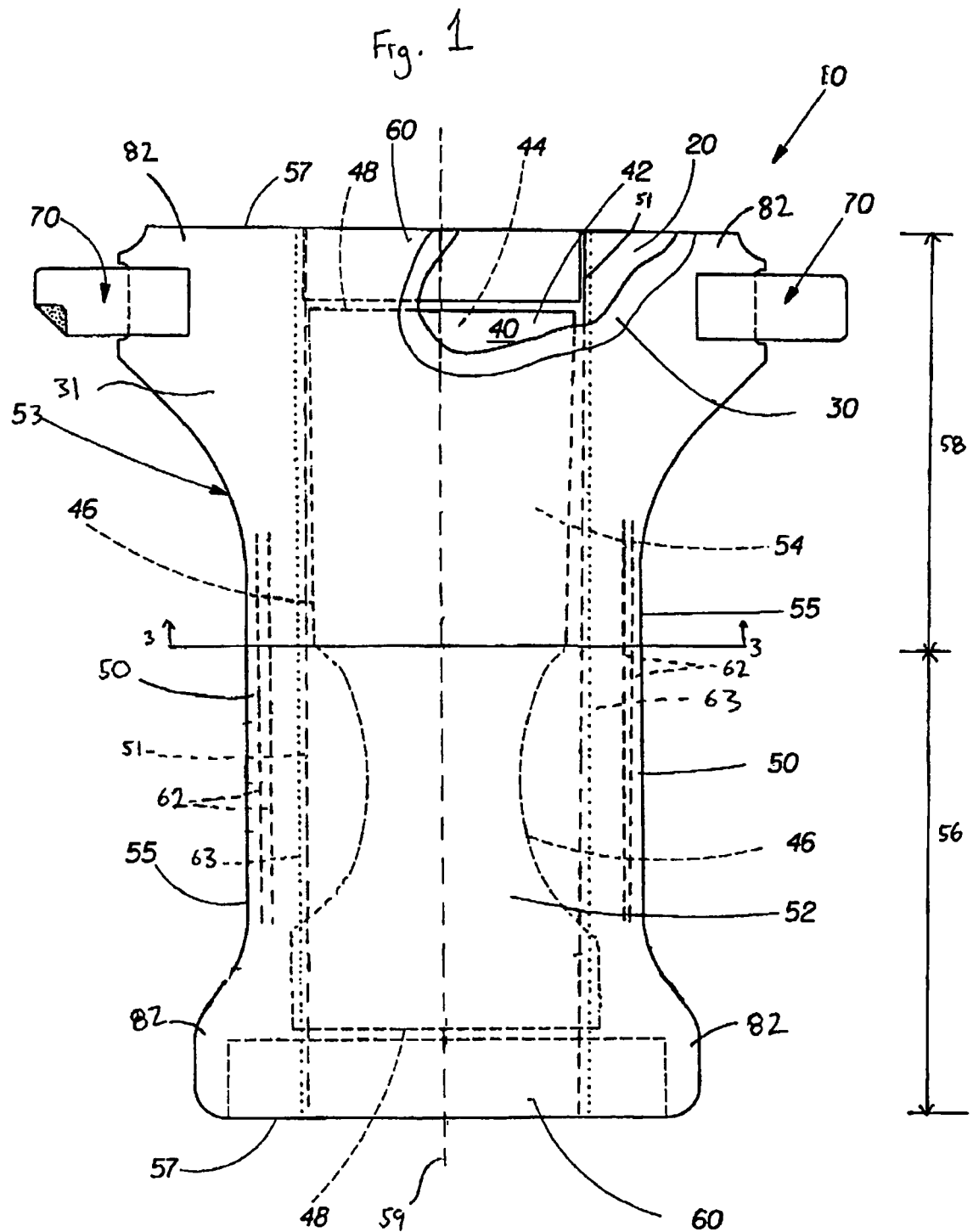
FIG. 1 shows a plan view of the absorbent article of the present invention.

For the present invention, detailed herein are various definitions which are intended to aid in the interpretation of the claimed subject matter.

As used herein, the term "absorbent article" refers to devices which absorb and contain body exudates, and more specifically, refers to devices which are placed against or in proximity to the body of the wearer to absorb and contain the various exudates discharged from the body. Such devices include, but are not limited to, diapers, training pants, adult incontinence products, sanitary napkins, and pantiliners.

As used herein, the term "diaper" refers to an absorbent article generally worn by infants, and incontinent persons about the lower torso of the wearer. In other words, the term "diaper" includes infant diapers, training pants, adult incontinence devices, etc.

As used herein, the term "disposable" refers to absorbent articles which generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "telomer" refers to an addition polymer, usually of low molecular weight, in which the growth of molecules is terminated by a radical-supplying chain transfer agent or a low molecular weight polymer in which the terminal group on the end of the chain-like molecule is not the same as the side group. Telomer may also be used synonymously with oligomer, which is a polymer with very few (two to ten) repeating units.

As used herein, the term "disposed" is used to mean that an element(s) of the absorbent article is formed (joined, positioned, or applied) in a particular place or position as a unitary structure with other elements of the article or as a separate element joined to another element of the article.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, "interior surface" or "body surface" means a surface of the article or component which is intended to be worn toward or adjacent to the body of a wearer.

As used herein, "exterior surface" or "garment surface" means a surface of the article or component which is on the opposite side of the interior surface and is intended to be worn toward or placed adjacent to the wearer's undergarments or clothing when the absorbent article is worn.

As used herein, "low surface tension fluids" refers to fluids having a surface tension of less than about 72 dynes/cm, preferably less than about 60 dynes/cm, and even more preferably less than about 60 dynes/cm, and most preferably from about 25 to about 55 dynes/cm.

As used herein, the term "flexible" refers to materials which are compliant and that readily conform to the general shape and contours of the human body.

All percentages, ratios and proportions used herein are by weight unless otherwise specified.

Absorbent Article

The disposable absorbent articles of the present invention may comprise a liquid pervious topsheet, a backsheet attached or joined to the topsheet, and an absorbent core positioned between the topsheet and the backsheet. Disposable absorbent articles and components thereof, including the topsheet, backsheet, absorbent core, and any individual layers of these components, generally have an interior surface (or body surface) and an exterior surface (or garment surface).

The following description generally discusses the absorbent core, first topsheet, and backsheet materials that are useful in disposable absorbent articles. It is to be understood that this general description applies to the components of the specific absorbent article shown in FIGS. 1-4, which are further described below, and to other disposable absorbent articles which are generally described herein.

Figure 2:
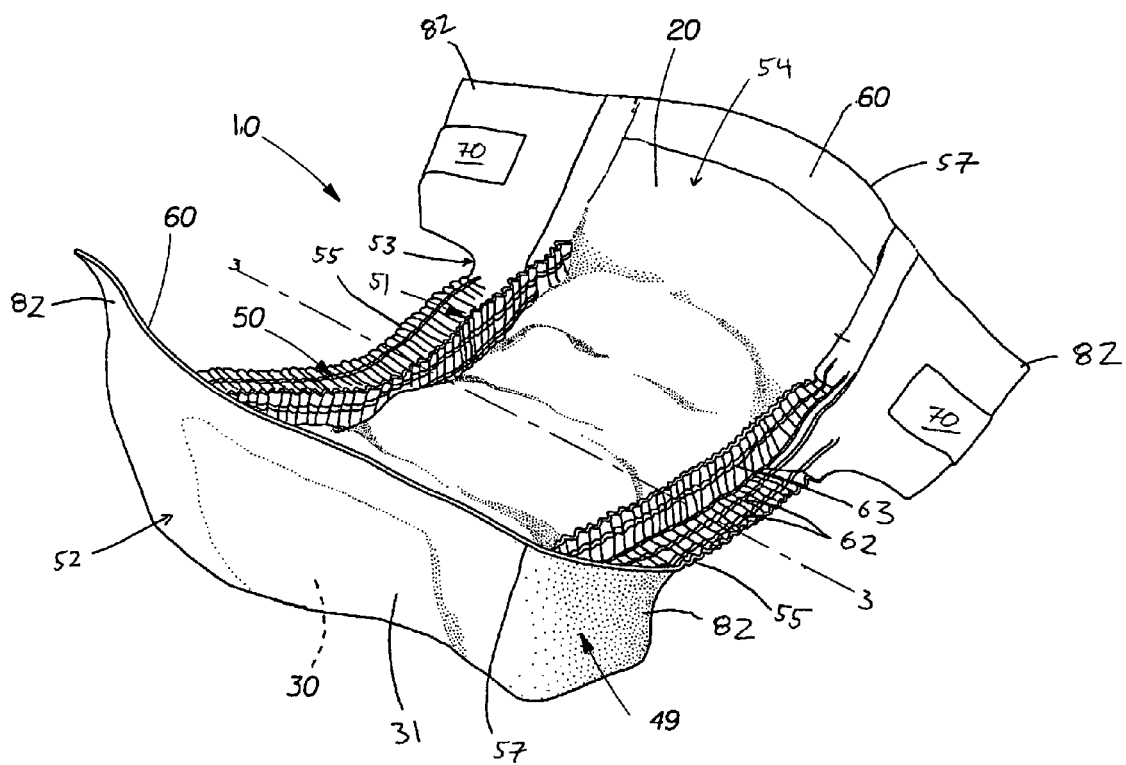
FIG. 2 shows a perspective view of an absorbent article of the present invention.

FIG. 1 is a plan view of the diaper 10 of the present invention in its flat-out, uncontracted state (i.e., with elastic induced contraction pulled out) with portions of the structure being cut-away to more clearly show the construction of the diaper 10. The portion of the diaper 10 which faces away from the wearer, the outer surface, is oriented towards the viewer. FIG. 2 is a perspective view of the diaper 10 in a partially contract state. As shown in FIG. 1, the diaper 10 may comprise a liquid pervious first topsheet 20; a liquid impervious backsheet 30 joined with the topsheet 20; an absorbent core 40 positioned between the first topsheet 20 and the backsheet 30, the absorbent core 40 having a exterior surface (or garment facing surface) 42, an interior surface (or a body facing surface) 44, side edges 46, and waist edges 48. The diaper 10 may further comprise a gasketing cuff 50 and a barrier cuff 51. The diaper 10 may comprise an elastic waist feature multiply designated as 60 (also referred to herein as a waistband or belt) and a fastening system generally multiply designated as 70.

The diaper 10 is shown in FIG. 1 to have an outer surface 52, an inner surface 54 opposed to the outer surface 52, a first waist region 56, a second waist region 58, and a periphery 53 which is defined by the outer edges of the diaper 10 in which the longitudinal edges 55 and the end edges 57. (While the skilled artisan will recognize that a diaper is usually described in terms of having a pair of waist regions and a crotch region between the waist regions, in this application, for simplicity of terminology, the diaper 10 is described as having only waist regions including a portion of the diaper which would typically be designated as part of the crotch region). The inner surface 54 of the diaper 10 comprises that portion of the diaper 10 which is positioned adjacent to the wearer's body during use (i.e., the inner surface 54 generally is formed by at least a portion of the first topsheet 20 and other components that may be joined to the first topsheet 20). The outer surface 52 comprises that portion of the diaper 10 which is positioned away from the wearer's body (i.e., the outer surface 52 generally is formed by at least a portion of the backsheet 30 and other components that may be joined to the backsheet 30). The first waist region 56 and the second waist region 58 extend, respectively, from the end edges 57 of the periphery 53 to the lateral centerline (sectional line 3-3) of the diaper 10. FIG. 1 also shows the longitudinal centerline 59.

FIG. 2 shows a perspective view of the article of the present invention which includes at least a first and second cuff wherein the backsheet and at least one of the additional components has been treated with the hydrophobic surface coating. FIG. 3 merely depicts a cross-sectional view of the diaper shown in FIG. 2.

Absorbent Core

The absorbent core 40 may take on any size or shape that is compatible with the diaper 10. In one embodiment, the diaper 10 has an asymmetric, modified T-shaped absorbent core 40 having a narrowing of the side edge 46 in the first waist region 56 but remaining generally rectangular-shaped in the second waist region 58. Absorbent core construction is well known in the art. Exemplary absorbent structures for use as the absorbent core of the present invention that have achieved wide acceptance and commercial success are described in U.S. Pat. Nos. 4,610,678, 4,673,402, 4,888,231, and 4,834,735. The absorbent core may further comprise the dual core system containing an acquisition/distribution core of chemically stiffened fibers positioned over an absorbent storage core as detailed in U.S. Pat. Nos. 5,234,423 and 5,147,345.

In general, the absorbent core 40 is capable of absorbing or retaining liquids (e.g., menses, urine, and/or other body exudates). The absorbent core 40 may be compressible, conformable, and non-irritating to the wearer's skin. The absorbent core 40 may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core 40 may also be varied (e.g., the absorbent core may have varying caliper zones and/or have a profile so as to be thicker in the center; hydrophilic gradients; gradients of the absorbent composite of the present invention, superabsorbent gradients; or lower average density and lower average basis weight zones, e.g., acquisition zones; or may comprise one or more layers or structures). The total absorbent capacity of the absorbent core 40 should be compatible with the design loading and the intended use of the absorbent article. Further, the size and absorbent capacity of the absorbent core 40 may be varied to accommodate different uses such as diapers, incontinence pads, pantiliners, regular sanitary napkins, and overnight sanitary napkins, and to accommodate wearers ranging from infants to adults. The absorbent core 40 can include other absorbent components that are often used in absorbent articles, for example, a dusting layer, a wicking or acquisition layer, or a secondary topsheet for increasing the wearer's comfort.

Figure 3A:
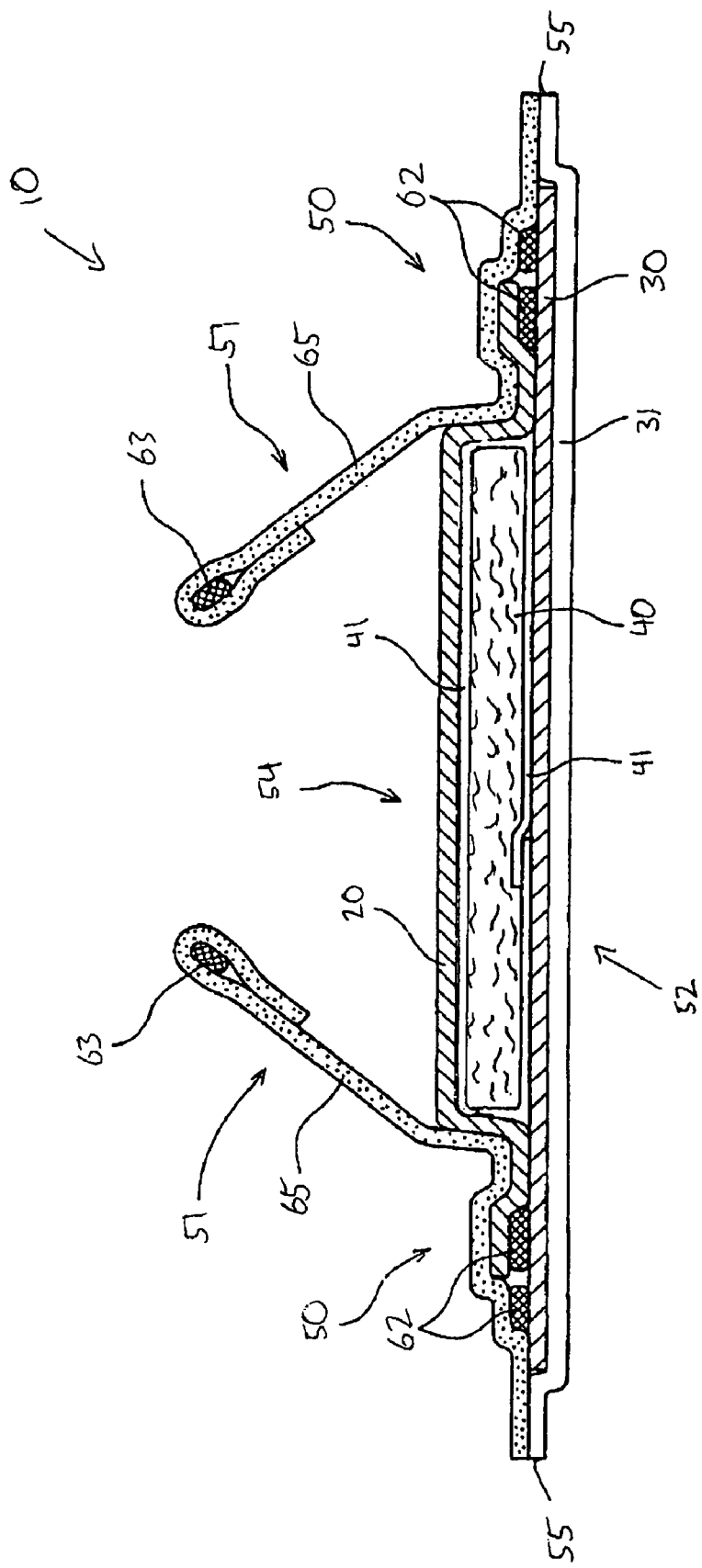
FIG. 3a is a cross-sectional view of the absorbent article as taken through sectional line 3-3 in FIG. 1 showing a cuff embodiment.
Figure 3B:
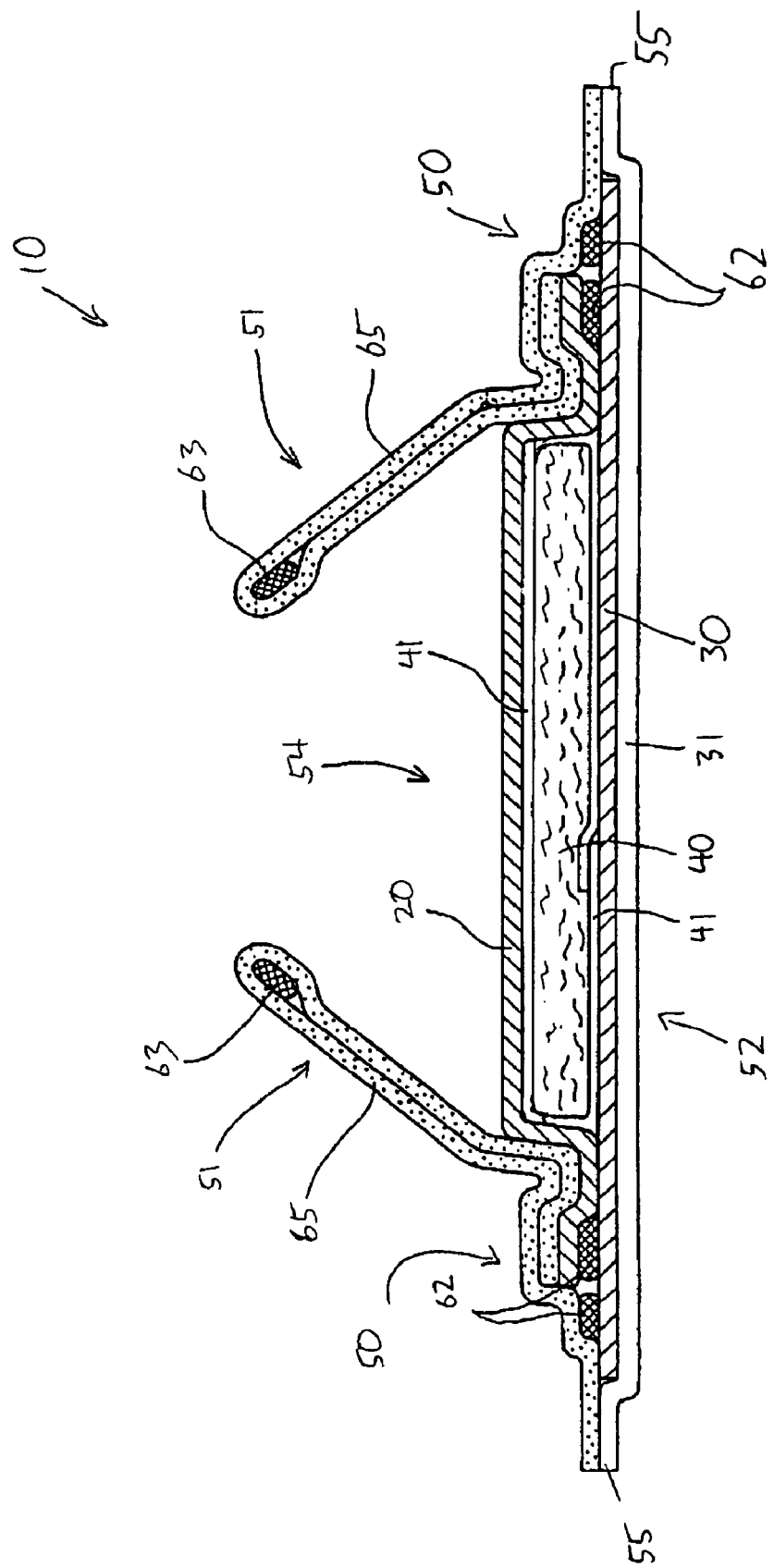
FIG. 3b is a cross-sectional view of the absorbent article as taken through sectional line 3-3 in FIG. 1 showing a cuff embodiment.
Figure 3C:
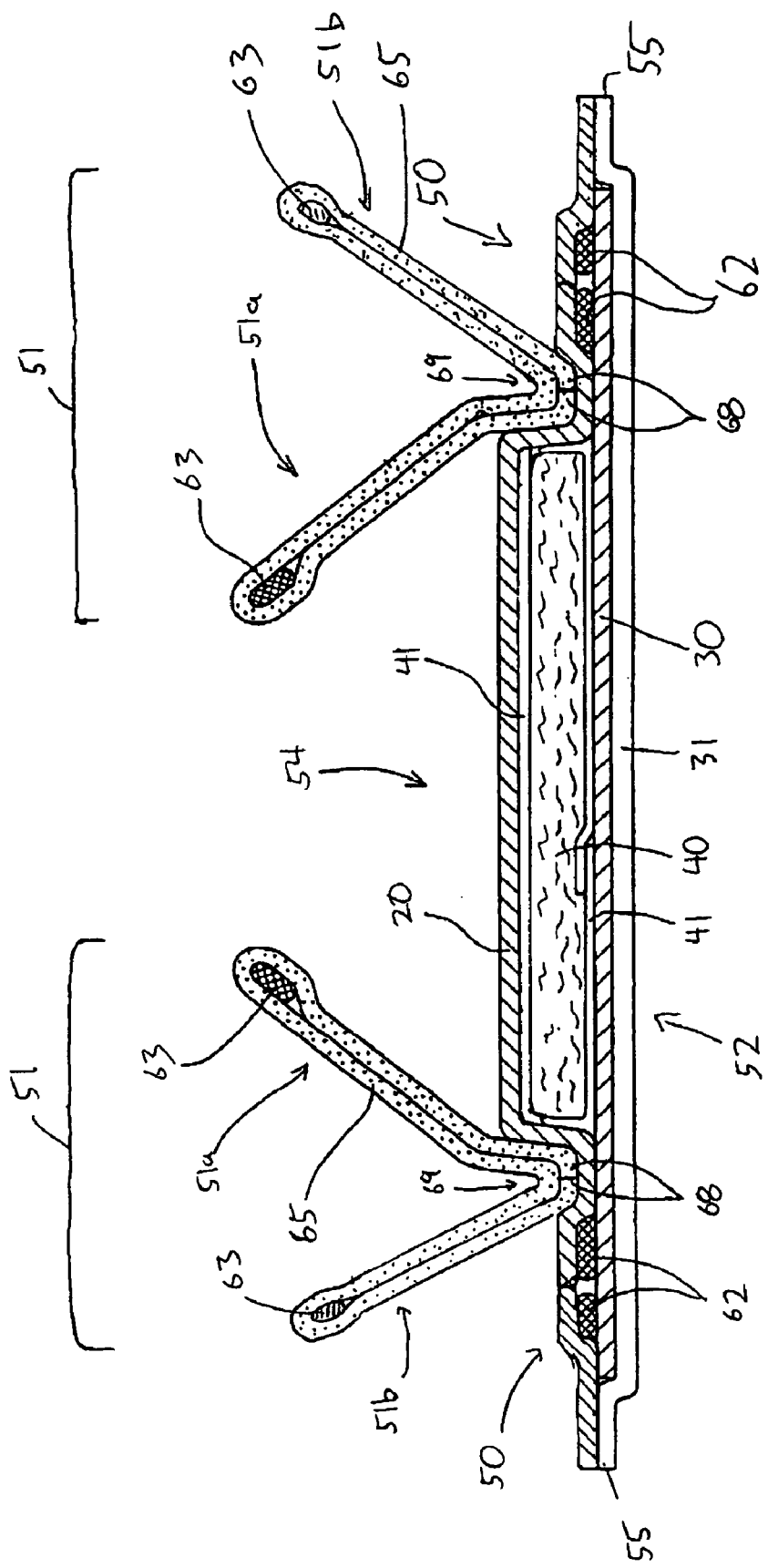
FIG. 3c is a cross-sectional view of the absorbent article as taken through sectional line 3-3 in FIG. 1 showing a cuff embodiment.

The absorbent core 40 may also comprise a core cover 41 (as shown in FIGS. 3a-c and described in detail below).

Topsheet

The first topsheet 20 of diaper 10 may be made of a hydrophilic material that promotes rapid transfer of liquids (e.g., urine, menses, and/or runny feces) through the topsheet 20. If the first topsheet 20 is made of a hydrophobic material, at least the upper surface of the topsheet may be treated to be hydrophilic so that liquids will transfer through the topsheet more rapidly. This diminishes the likelihood that body exudates will flow off the topsheet rather than being drawn through the topsheet and being absorbed by the absorbent core. The first topsheet 20 may be rendered hydrophilic by treating it with a surfactant. Suitable methods for treating the topsheet 20 with a surfactant include spraying the topsheet material with the surfactant and immersing the material into the surfactant. A more detailed discussion of such a treatment and hydrophilicity is contained in U.S. Pat. Nos. 4,988,344 and 4,988,345.

The topsheet 20 may be pliant, soft feeling, and non-irritating to the wearer's skin. Further, the topsheet is liquid pervious, permitting liquids (e.g., menses, urine, and/or runny feces) to readily penetrate through its thickness. A suitable topsheet 20 may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet 20 comprises a nonwoven web, the web may be manufactured by a wide number of known techniques. For example, the web may be spunbonded, carded, wet-laid, melt-blown, hydroentangled, combinations of the above, or the like. In certain embodiments, the topsheet 20 may comprise the light-weight nonwoven laminate with a hydrophobic surface coating disposed thereon, as described in greater detail below.

Backsheet

The backsheet 30 may be impervious to low surface tension fluids (e.g., menses, urine, and/or runny feces). The backsheet 30 may be manufactured from a thin plastic film, although other flexible liquid impervious materials may also be used. The backsheet 30 may prevent the exudates absorbed and contained in the absorbent core from wetting articles which contact the absorbent article such as bedsheets, pants, pajamas and undergarments. The backsheet 30 may comprise a woven or nonwoven material, polymeric films such as thermoplastic films of polyethylene or polypropylene, or composite materials such as a film-coated nonwoven material or a film-nonwoven laminate. A suitable backsheet 30 is a polyethylene film having a thickness of from about 0.012 mm (0.5 mils) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet 30 may be embossed and/or matte finished and provides a more cloth-like appearance. Further, the backsheet may permit vapors to escape from the absorbent core (i.e., the backsheet is breathable) while still preventing exudates from passing through the backsheet 30. The size of the backsheet 30 is dictated by the size of the absorbent core and the exact absorbent article design selected. In certain embodiments, backsheet 30 may comprise the light-weight nonwoven laminate with a hydrophobic surface coating disposed thereon, as described in greater detail below.

The backsheet 30 and the first topsheet 20 are positioned adjacent the garment surface and the body surface, respectively, of the absorbent core 40. The absorbent core 40 may be joined with the topsheet 20, the backsheet 30, or both in any manner as is known by attachment means such as those well known in the art. However, embodiments of the present invention are envisioned wherein portions of the entire absorbent core 40 are unattached to one or both of the topsheet 20 and the backsheet 30.

For example, the backsheet 30 and/or the first topsheet 20 may be secured to the absorbent core 40 or to each other by a uniform continuous layer of adhesive, a patterned layer of adhesive, or an array of separate lines, spirals, or spots of adhesive. Adhesives which have been found to be satisfactory are manufactured by Bostik-Findley of Milwaukee, Wis. under the designation HL-24012031. The attachment means may comprise an open pattern network of filaments of adhesive as is disclosed in U.S. Pat. No. 4,573,986. An exemplary attachment means of an open pattern network of filaments comprises several lines of adhesive filaments swirled into a spiral pattern such as illustrated by the apparatus and method shown in U.S. Pat. Nos. 3,911,173, 4,785,996, and 4,842,666. Alternatively, the attachment means may comprise heat bonds, pressure bonds, ultrasonic bonds, dynamic mechanical bonds, or any other suitable attachment means or combinations of these attachment means as are known in the art.

Other optional elements may include a fastening system 70, elasticized side panels 82, and a waist feature 60. The fastening system 70 allows for the joining of the first waist region 56 and the second waist region 58 in an overlapping configuration such that lateral tensions are maintained around the circumference of the diaper 10 to maintain the diaper on the wearer. Exemplary fastening systems 70 are disclosed in U.S. Pat. Nos. 4,846,815, 4,894,060, 4,946,527, 3,848,594, 4,662,875, and 5,151,092. In certain embodiments, a fastening system 70 may be omitted. In such embodiments, the waist regions 56 and 58 may be joined by the manufacturer to form a pant-type diaper having a preformed waist opening and leg openings (i.e., no end-user manipulation of the diaper is needed to form the waist opening and leg openings). Pant-type diapers are also commonly referred to as "closed diapers," "prefastened diapers," "pull-on diapers," "training pants," and "diaper-pants". Suitable pants are disclosed in U.S. Pat. Nos. 5,246,433, 5,569,234, 6,120,487, 6,120,489, 4,940,464, and 5,092,861. Generally, the waist regions 56 and 58 may be joined by a permanent or refastenable bonding method.

The diaper 10 may also comprise elasticized side panels 82 in the waist regions 56 and 58 to provide an elastically extensible feature that provides a more comfortable and contouring fit and more effective application of the diaper 10. The elasticized side panels 82 may be constructed in a number of configurations. Examples of diapers with elasticized side panels 82 are disclosed in U.S. Pat. Nos. 4,857,067, 4,381,781, 4,938,753, and 5,151,092.

The diaper 10 may also comprise an elasticized waist feature 60. The elasticized waist feature 60 may help the diaper to provide improved fit and containment. The elastic waist feature 60 is generally intended to elastically expand and contract to dynamically fit the wearer's waist. The elastic waist feature 60 may extend at least longitudinally outwardly from at least one waist edge 48 of the absorbent core 40 and generally forms at least a portion of the end edge 57 of the diaper 10. In certain embodiments, the diaper may have two elastic waist features, one positioned in the first waist region 56 and one positioned in the second waist region 58. Further, while the elastic waist feature 60 or any of its constituent elements may comprise one or more separate elements affixed to the diaper 10, the elastic waist feature 60 may be constructed as an extension of other elements of the diaper 10, such as the backsheet 30, the topsheet 20, or both the backsheet 30 and the topsheet 30. The elastic waist feature 60 may be constructed in a number of different configurations including those described in U.S. Pat. Nos. 4,515,595, 4,710,189, 5,151,092, and 5,221,274.

Barrier Members

In a certain embodiments, the diaper 10 may further comprise at least one barrier member. Barrier members are physical structures joined or applied to the diaper 10 to improve the barrier properties of the diaper 10. Barrier members include, but are not limited to, structures such as a core cover, an outer cover, a barrier cuff, a gasketing cuff, an elasticized topsheet, and combinations thereof. It may be desirable that the barrier member comprise the light-weight nonwoven laminate with the hydrophobic surface coating disposed thereon, as described in greater detail below.

The diaper 10 may include one or more gasketing cuffs 50 which may provide improved containment of liquids and other body exudates. Gasketing cuffs 50 may also be referred to as outer leg cuff, leg bands, side flaps, leg cuffs, or elastic cuffs. U.S. Pat. No. 3,860,003 describes a disposable diaper which provides a contractible leg opening having a side flap and one or more elastic members to provide an elasticized leg cuff. Elasticity may be imparted to gasketing cuff 50 by one or more elastic members 62. Additionally, diaper 10 may include one or more barrier cuffs 51 which also provide improved containment of liquids and other body exudates. Barrier cuffs 51 may also be referred to as barrier leg cuffs, inner leg cuffs, or "stand-up" elasticized flaps. U.S. Pat. Nos. 4,808,178 and 4,909,803 issued to Aziz et al. on Feb. 28, 1989 and Mar. 20, 1990, respectively, describe disposable diapers having "stand-up" elasticized flaps that improve the containment of the leg regions. As with gasketing cuffs 50, barrier cuffs 51 may also include one or more elastic members 63. Elastic member 63 may provide elasticity to the barrier cuff 51 which may aid in keeping barrier cuff 51 in a "stand-up" position.

Gasketing cuff 50 and barrier cuff 51 may both be provided by way of an integral cuff, as exampled in U.S. Pat. Nos. 4,695,278 and 4,795,454 issued to Lawson on Sep. 22, 1987 and to Dragoo on Jan. 3, 1989, respectively. Additional cuffs may be provided in an article of the present invention as detailed in US Statutory Invention Registration H1630, which published Jan. 7, 1997.

FIGS. 3a-c depict a cross-sectional view of the diaper shown in FIG. 1 taken along sectional line 3-3. FIGS. 3a-c depict exemplary cuff construction; however, modifications can be made to the cuff construction without departing from the spirit and scope of the invention. A gasketing cuff 50 and barrier cuff 51 are both shown in FIGS. 3a-c, but a single cuff design is equally feasible. FIG. 3a illustrates an exemplary gasketing cuff 50 and barrier cuff 51 construction. Both cuffs 50, 51 may share a common substrate 65 along one of their interior and/or exterior surfaces. Barrier cuff 51 is shown in a single layer configuration where over a substantial portion of the lateral width the cuff 51 comprises a single ply of the substrate 65. FIG. 3b illustrates an exemplary gasketing cuff 50 and barrier cuff 51 construction with the barrier cuff 51 in a multiple layer configuration. In the multiple layer construction, at least two plys of the substrate exist over a substantial portion of the lateral width of the cuff 51. It would be obvious to those skilled in the art that one or more elastic members 62, 63 may be used in each gasketing cuff 50 and/or barrier cuff 51, respectively, without departing from the scope of this invention. Furthermore, it would be obvious to those skilled in the art that the exact configuration of the substrate 65 can be altered without departing from the scope of this invention.

FIG. 3c illustrates an exemplary dual barrier cuff 51 design having a first barrier cuff 51a and a second barrier cuff 51b. The barrier cuff 51 may include a substrate 65 that forms portions of both the first barrier cuff 51a and the second barrier cuff 51b. The first barrier cuff 51a may be positioned nearer to the longitudinal centerline 59 (shown in FIG. 1) than the second barrier cuff 51b, which may be positioned nearer to the longitudinal edges 55 of the diaper 10. The substrate 65 may envelop an elastic member 63 that may be present in first barrier cuff 51a and/or the second barrier cuff 51b. Generally, the first barrier cuff 51a and the second barrier cuff 51b contain at least one elastic member 63 enveloped within the substrate 65. The substrate 65 may have two edges multiply designated 68. The edges 68 may be joined together at a bond site 69. The edges 68 may be configured in an abutting manner as shown in FIG. 3c; however, other configurations are feasible including configuring the edges 68 in an overlapping manner. In certain embodiments, the bond site 69 may also serve to join the barrier cuff 51 to the diaper 10. Bonding may be performed by any means known in the art including adhesive, pressure, ultrasonic, and heat bonding.

A variety of suitable materials may be used as the substrate 65 in the cuffs described above. Suitable embodiments of the present invention may have the substrate 65 comprising the light-weight nonwoven laminate with a hydrophobic surface coating disposed thereon, as described in greater detail below.

In certain embodiments of the dual cuff design, the substrate 65 may be continuous. Dual barrier cuffs 51 made from a continuous or discontinuous substrate 65 are more fully described in the pending U.S. patent application Ser. No. 10/824,122 filed on Apr. 14, 2004 in the name of Ashton et al. A continuous substrate 65 is shown in FIG. 3c. The substrate 65 forms a continuous path from one edge 68 to the other edge 68. Along the continuous path, the structure of the first barrier cuff 51a and the second barrier cuff 61b may be formed and the elastic members 63 may be enveloped. The edges 68 may be attached to each other and/or to the diaper 10 at a common bond site 69.

As shown in FIGS. 3a-c, a core cover 41 may be included in certain embodiments of the diaper 10. The core cover 41 may provide structural integrity to the core 40. The core cover 41 may contain the core 40 components such as cellulosic material and absorbent gelling material, which both may tend to migrate, move, or become airborne without a physical barrier. The core cover 41 may entirely envelop the core 40, as shown in FIGS. 3a-b, or may only partially cover the core 40. The core cover 41 generally comprises a nonwoven material. In certain embodiments, the core cover 41 comprises the light-weight nonwoven laminate with a hydrophobic surface coating disposed thereon, as described in greater detail below.

In certain embodiments, the diaper 10 may comprise an outer cover 31. The outer cover 31 generally covers substantially all of the exterior surface of the diaper 10. In some embodiments, the outer cover 31 is coterminous with the backsheet 30. The outer cover 31 may be bonded to a portion of the backsheet 30 to form a laminate structure. Bonding may be performed by any means known in the art including adhesive bonding and heat bonding. The outer cover 31 may be utilized to provide extra strength or bulk to the diaper 10. Outer covers 31 are often used to improve the aesthetic quality of exterior surface of the diaper 10. It is desirable that the exterior surface of the diaper 10 exhibit a cloth-like look and feel. Various materials are suitable for use as the outer cover 31. Such materials include woven webs, foams, scrims, films, and loose fibers. However, in certain embodiments of the present invention, the outer cover 31 may be constructed to provide increased barrier protection. In certain embodiments, the outer cover 31 comprises the light-weight nonwoven laminate with a hydrophobic surface coating disposed thereon, as described in greater detail below. Use of the light-weight nonwoven laminate with the hydrophobic surface-coating disposed thereon is believed to provide the requisite aesthetic benefits of a cloth-like look and feel while also providing increased barrier protection with a lower basis weight and lower cost material.

Figure 4:
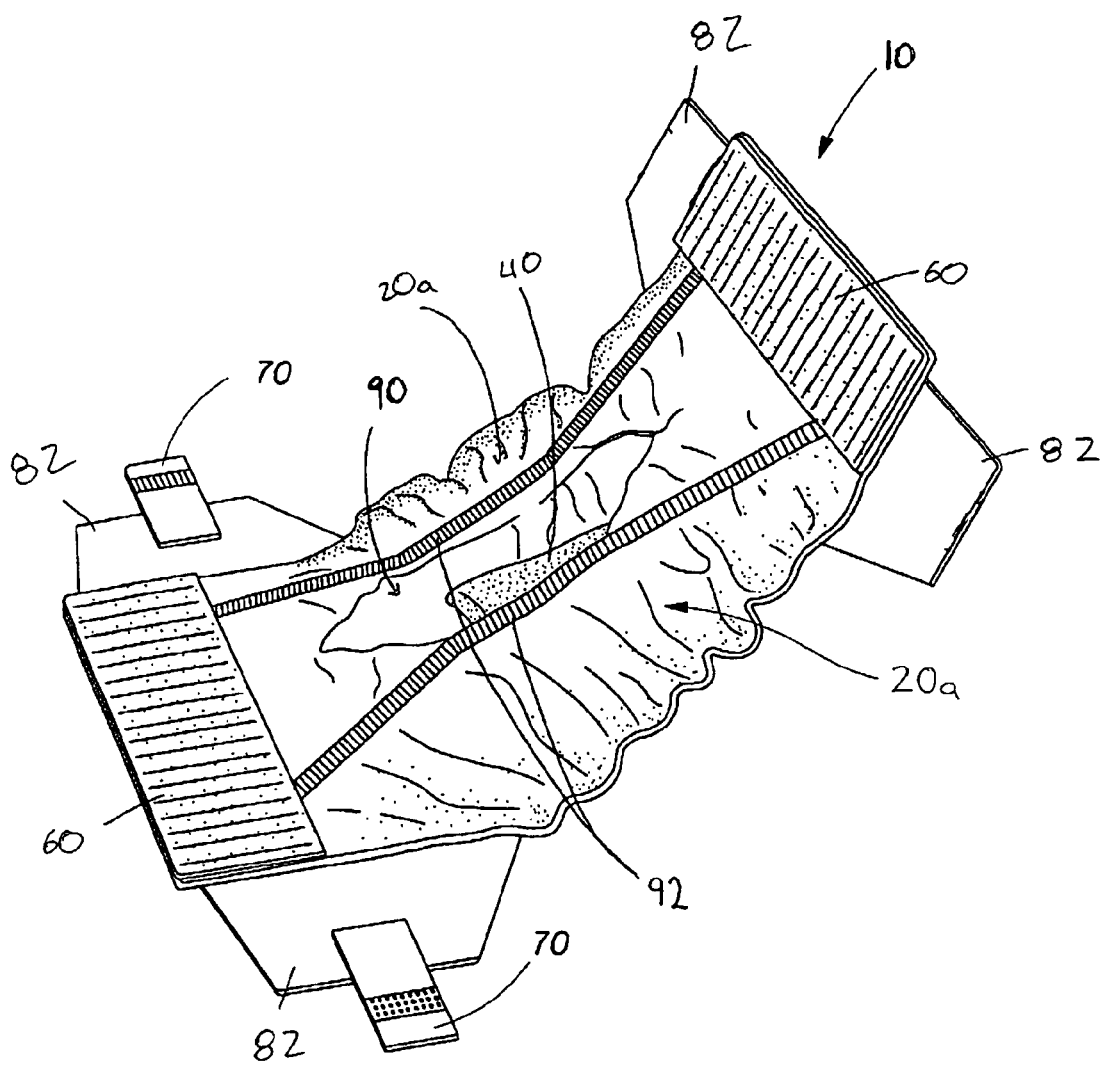
FIG. 4. shows a perspective view of absorbent article of the present invention having an elasticized topsheet.

In certain embodiments, the diaper 10 may comprise a topsheet that is elasticized to provide storage compartments for body exudates, particularly bowel movements. FIG. 4 shows an exemplary elasticized topsheet. Such elasticized topsheets 20a and articles containing them are detailed in U.S. Pat. No. 6,482,191. FIG. 4 shows the elasticized topsheet 20a comprising an elongate slit opening 90 and a pair of elastic members 92. The elongate slit opening 90 allows passage of body exudates into the interior of the diaper 10. The elastic members 92 provide sufficient tension to the elasticized topsheet 20a so that the topsheet 20a will not sag while in use. While the elasticized topsheet 20a may be comprise any of the material listed above in regard to topsheets, it desirable that the elasticized topsheet 20a exhibit some degree of hydrophobicity. A hydrophobic elasticized topsheet 20a may prevent body exudates stored within the diaper 10 from seeping through the elasticized topsheet 20a and contacting the wearer's skin. In particularly suitable embodiments, the elasticized topsheet 20a comprises the light-weight nonwoven laminate with a hydrophobic surface coating disposed thereon, as described in greater detail below. Other possible configurations include the diaper 10 having a dual topsheet system of an elasticized topsheet and a second topsheet in a face-to-face planar relationship with the elasticized topsheet being the inner surface 54 of the diaper 10.

Light-Weight Nonwoven Laminate

Figure 5:
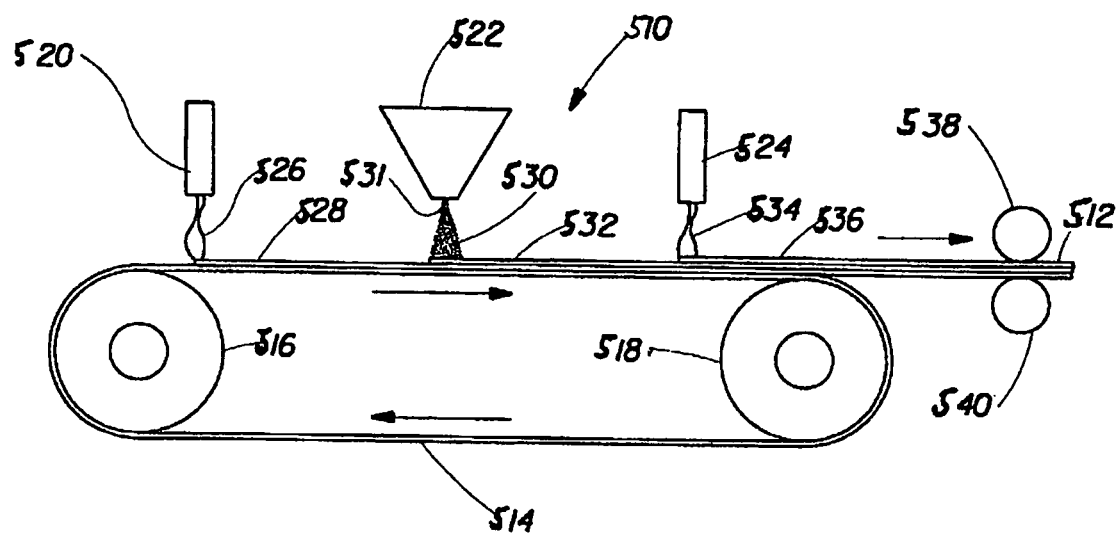
FIG. 5 is a schematic diagram of a forming machine that is used in making the light-weight nonwoven laminate of the present invention.

Nonwoven material and nonwoven laminate formation is well known in the art. FIG. 5 shows a schematic representation of a forming machine 510 which may be used to produce the light-weight nonwoven laminate 512. The forming machine 510 may have an endless forming belt 514 wrapped around rollers 516, 518 so that the belt 514 is driven in the direction shown by the arrows. The forming machine 510 may include three stations: a first continuous filament station 520, a fine fiber station 522, and a second continuous filament station 524. However, it should be understood that more than three forming stations may be utilized to build up layers of higher basis weight. Alternatively, each of the laminate layers may be formed separately, rolled, and later converted to the fabric laminate off-line. In addition, the fabric laminate 512 could be formed of more than or less than three layers depending on the requirements for the particular end use for the fabric laminate 512. For example, for some applications it may be desirable to have at least two inner meltblown layers for improved performance and for extremely lightweight applications a two-layer laminate may be made.

The first and second continuous filament stations 520, 524 may be conventional spunbond extruders with spinnerets, which form continuous filaments of a polymer and deposit those filaments onto the forming belt 514 in a generally random interlaced fashion. The continuous filament stations 520 and 524 may include one or more spinnerets heads depending on the speed of the process and the particular polymer being used. Suitable polymers include, but not limited to, polyolefins such as polypropylene and polyethylene, polyester, polyamide, polyimide, polyactic acid, polyhydroxyalkanoate, polyvinyl alcohol, polyacrylates, and combinations thereof. During the formation process, the polymer is continuously extruded through the spinneret to form discrete filaments. The filaments may be drawn either mechanically or pneumatically to molecularly orient the polymer filaments and improve tensile characteristics. Forming spunbonded material is conventional in the art, and the design of such a spunbonded forming station is thought to be well within the ability of those of ordinary skill in the art. The nonwoven continuous filament webs 528 and 536 are prepared in conventional fashion such as illustrated by U.S. Pat. Nos. 3,692,618 3,338,992, 3,341,394, 3,502,538, 3,502,763, 3,909,009, 3,542,615, 3,802,817, and 4,340,563. Other methods for forming a nonwoven web having continuous filaments of a polymer are contemplated for use with the present invention.

The first continuous filament station 520 may produce first continuous filaments 526 that may be deposited on the forming belt 514 in a substantially random manner to form a first continuous filament layer 528.

The fine fiber station 522 consists of a die 531 which is used to form fine fibers 530. In certain embodiments, the fine fibers 530 are meltblown fibers. In a meltblown process, a thermoplastic polymer exits the die 531 and a high pressure fluid, usually air, attenuates and spreads the polymer stream to form fine fibers 530. Suitable polymers include, but not limited to, polyolefins such as polypropylene and polyethylene, polyester, polyamide, polyimide, polyactic acid, polyhydroxyalkanoate, polyvinyl alcohol, polyacrylates, and combinations thereof. The fine fibers 530 are randomly deposited on top of the first continuous filament layer 528 and form a fine fiber layer 532. The construction and operation of the fine fiber station 522 for forming fine fibers 530 and the fine fiber layer 532 is considered conventional and well within the ability of those of ordinary skill in the art. Such skill is demonstrated by NRL Report 4364, "Manufacture of Super-Fine Organic Fibers", by V. A. Wendt, E. L. Boon, and C. D. Fluharty; NRL Report 5265, "An Improved Device for the Formation of Super-Fine Thermoplastic Fibers", by K. D. Lawrence, R. T. Lukas, and J. A. Young; and U.S. Pat. No. 3,849,241. Other methods for forming a nonwoven web of fine fibers including nanofibers are contemplated for use with the present invention.

After the fine fiber layer 532 has been deposited by the fine fiber station 522 onto the first continuous filament layer 528, the second continuous filament station 524 may produce second continuous filaments 534 which are deposited in random orientation on top of the fine fiber layer 532 to produce a second continuous filament layer 536.

The resulting light-weight nonwoven laminate 512 may be fed through bonding rolls 538 and 540. The surfaces of one or both of the bonding rolls 538 and 540 are provided with a raised pattern such as spots or grids. The bonding rolls may be heated to the softening temperature of the polymer used to form the layers of the nonwoven laminate 512. As the nonwoven laminate 512 passes between the bonding rolls 538 and 540, the material may be compressed and heated by the bonding rolls in accordance with the pattern on the rolls to create a pattern of discrete bonds 541, as shown in FIG. 5. The bonds 541 may provide bonding from layer-to-layer and bonding with respect to the particular filaments and/or fibers within each layer. Methods for forming bonds 541 are well-known in the art and can be carried out as described by means of heated rolls or by means of ultrasonic heating of the nonwoven laminate 512 to produced discrete area thermally bonded filaments, fibers, and layers. In certain embodiments and in accordance with conventional practice described in U.S. Pat. No. 4,041,203, it is desirable for the fibers (e.g., meltblown fibers) of the fine fiber layer to fuse within the bond areas while the continuous filaments (e.g., spunbond filaments) of the continuous filament layers retain their integrity in order to achieve good strength characteristics.

Figure 6:
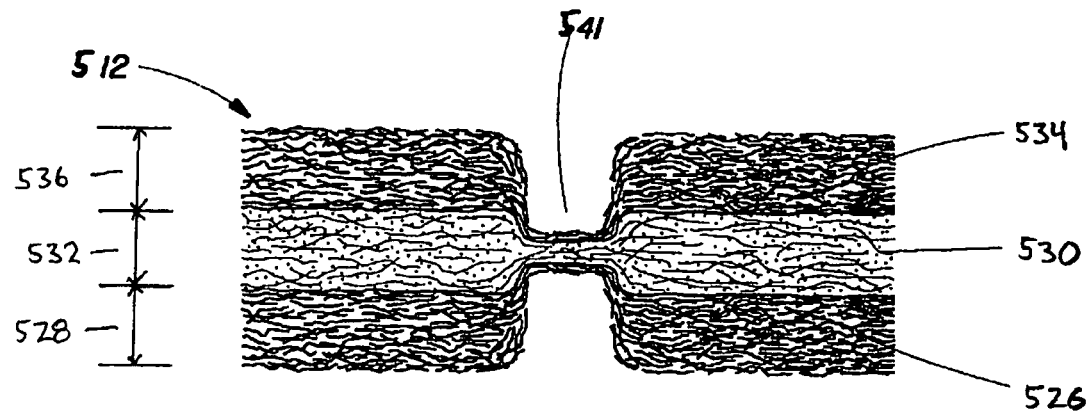
FIG. 6 is a cross-sectional view of the light-weight nonwoven laminate of the present invention.

FIG. 6 is a representation cross-sectional view of the nonwoven laminate 512 showing the first continuous filament layer 528 made of first continuous filaments 526, the fine fiber layer 532 made of fine fibers 530, and the second continuous filament layer 536 made of second continuous filaments 534. The bond 541 may compress the nonwoven laminate 512 and may fuse layers together and fibers and/or filaments together.

The continuous filaments 526 and 534 may be formed with a range of diameters. In certain embodiments, the continuous filaments 526 and 534 have an average diameter in the range of from about 12 microns to about 30 microns. Likewise, basis weights of the continuous filaments layers 528 and 536 may be varied. In certain embodiments, basis weights for each continuous filament layers 528 and 536 may range from about 2 grams/meter$^2$ (gsm) to about 20 gsm. In other suitable embodiments, basis weights of the continuous filaments layers 528 and 536 each may range from about 4 gsm to about 10 gsm. In other embodiments, basis weights of the continuous filaments layers 528 and 536 each may range from about 5 gsm to about 8 gsm. The first continuous filaments layer 528 and the second continuous filaments layer 536 need not have the same basis weight. Additionally, the first continuous filaments 526 and the second continuous filaments 534 need not have the same diameter.

The fine fibers 530 may be formed with a range of diameters. In certain embodiments, the fine fibers 530 have an average diameter in the range of less than about 12 microns. In other embodiments, the fine fibers have average diameter of less than about 5 microns. The fine fiber layer 532 has a basis weight of less than about 1.5 gsm. In certain embodiments, the basis weight of the fine fiber layer 530 is less than about 1.4 gsm. In certain embodiments, the basis weight of the fine fiber layer 530 is less than about 1.2 gsm. In certain embodiments, the basis weight of the fine fiber layer 530 is less than about 1.1 gsm. In other suitable embodiments, the basis weight of the fine fiber layer 532 is about 1.0 gsm or less.

In certain embodiments of the present invention, the total basis weight for the light-weight nonwoven laminate 512 should not exceed 45 gsm. In other embodiments, the total basis weight for the light-weight nonwoven laminate 512 should not exceed 30 gsm. In other embodiments, the total basis weight for the light-weight nonwoven laminate 512 should not exceed 20 gsm. Various basis weight combinations for the first continuous filaments layer 528, the fine fiber layer 532, and the second continuous filaments layer 536 are within the scope of this invention and should be readily appreciated by a skilled artisan. A suitable combination of basis weights for the first continuous filaments layer 528, the fine fiber layer 532, and the second continuous filaments layer 536 may be about 6 gsm to about 8 gsm; about 1.0 gsm; and about 6 gsm to about 8 gsm, respectively.

Hydrophobic Surface Coating

The disposable absorbent articles of the present invention additionally comprise a hydrophobic surface coating that may be disposed on at least one surface of the light-weight nonwoven laminate, which may be incorporated in a variety of barrier members. This hydrophobic surface coating comprises one or more silicone polymers and is also substantially free of aminosilicones.

Suitable silicone polymers are selected from the group consisting of silicone MQ resins, polydimethysiloxanes, crosslinked silicones, silicone liquid elastomers, and combinations thereof. Typically, the molecular weight of such silicone polymers should be at least about 4000 MW. However, the molecular weight of such silicone polymers may be at least about 10,000 MW, at least about 15,000 MW, at least about 20,000 MW, or at least about 25,000 MW. Suitable polydimethylsiloxanes are selected from the group consisting of vinyl-terminated polydimethsiloxanes, methyl hydrogen dimethylsiloxanes, hydroxyl-terminated polydimethysiloxanes, organo-modified polydimethylsiloxanes, and combinations thereof.

Alternatively, fluorinated polymers may also be used. Suitable fluorinated polymers are selected from the group consisting of telomers and polymers containing tetrafluoroethylene and/or perfluorinated alkyl chains. For instance, fluorinated surfactants, which are commercially available from Dupont under the tradename Zonyl®, are suitable for use herein. In particular, Zonyl® 321, 329, 8740, 9027, and 9360 are well suited for use in the present invention. Additionally, other Zonyl® materials include fluroadditives like micro-powders may be useful herein. These include, but are not limited to Zonyl® MP1100, MP1200, MP1400, MP1500J, MP1600N, TE-3667N (which is a water dispersion).

These materials may be deposited onto the surface of the light-weight nonwoven laminate of the present invention in amounts of from at least about 1 µg of coating per 1 g of a laminate. A suitable amount of silicone polymer present on the surface may be at least about 100 µg/g. In certain embodiments, the amount of silicone polymer present on the surface may be at least about 200 µg/g. In other suitable embodiments, the amount of silicone polymer present on the surface may be at least about 300 µg/g or at least about 400 µg/g.

Figure 7:
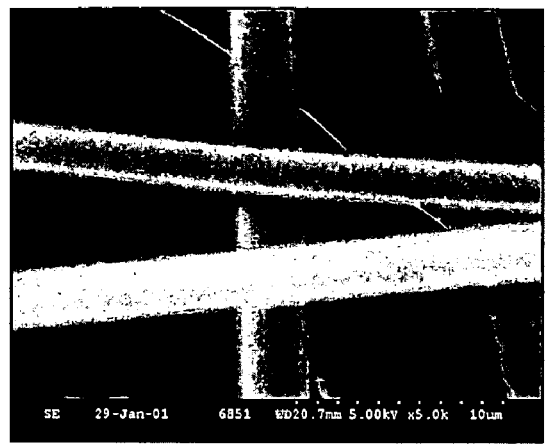
FIG. 7. illustrates a component of the present article prior to treatment with the hydrophobic surface coating of the present invention.
Figure 8:
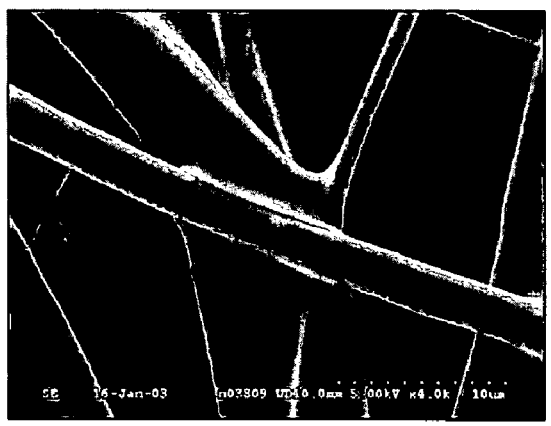
FIG. 8 illustrates a component of an article of the present invention that has been treated with a hydrophobic surface coating according to the present invention.
Figure 9:
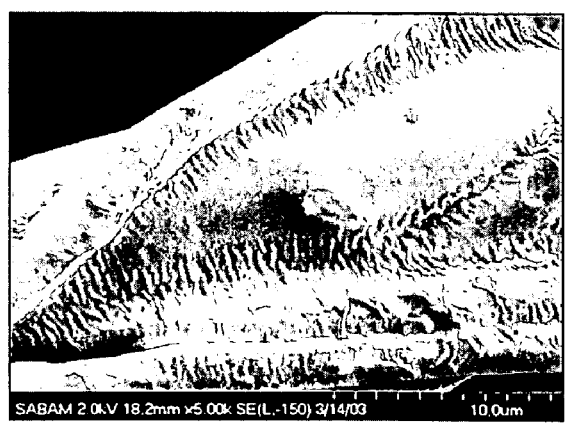
FIG. 9 illustrates a component of an article of the present invention that has been treated with another hydrophobic surface coating according to the present invention.

Without being limited by theory, Applicants have found that these hydrophobic surface coatings, when applied to various absorbent article components, tend to envelope or at least partially coat one or more fibrous structures of the component in such a way that a cohesive, uniform film-like network is formed around the fibrous structures, and partially fills the pore network of the fibrous structures. This film-like network serves to increase the barrier properties of the component, particularly when exposed to low surface energy fluids. The film-like network is illustrated in FIGS. 7, 8, and 9. In FIG. 7, an uncoated 15 gsm fibrous meltblown nonwoven is depicted. In FIG. 8, the nonwoven of FIG. 7 has been treated with a hydrophobic surface coating known as PSA950, which is commercially available from GE Silicones. PSA950 is a pressure sensitive adhesive which is a phenyl siloxane in solvent. Here, the film-like network has formed between the fibrous structures of the nonwoven. Likewise, in FIG. 9, the uncoated meltblown nonwoven of FIG. 7 is coated with a hydrophobic surface coating known as C2-0563 fabric water repellant, which is commercially available from Dow Corning. Again, it is clear that a film-like network is formed between the fibers and in the pores of the nonwoven, thereby improving its barrier properties. Additional description regarding the preparation of and the properties of the hydrophobic surface coating may be found in U.S. patent application Ser. No. 11/055,743 entitled "Hydrophobic Surface Coated Absorbent Article and Associated Methods," which was filed on Feb. 10, 2005 in the name of Kemal Catalan and which claims priority to U.S. Pat. App. No. 60/543,785 filed Feb. 11, 2004.

In certain embodiments of the present invention, the coating may be inherently elastomeric. Accordingly, when deposited onto one or more surfaces of an absorbent article component, the hydrophobic surface coating may additionally provide an elastic character to the article component when stretched.

Additionally, although it is envisioned that the present invention is primarily directed to absorbent personal care articles, it is easily foreseeable that the hydrophobic surface coatings disclosed herein may also be disposed onto substrates utilized for other purposes. For instance, treated substrates could be utilized in the manufacture of various surgical or medical materials (e.g., gowns, drapes, shoe covers, and caps), wipes (e.g., for car cleaning, lens cleaning, packaging, wet cleaning, and dust), consumer clothing, etc.

Moreover, it is important to note that when the coating is deposited onto the article component, it is preferred that the component is substantially free of polymers containing melt additives selected from the group consisting of polydimethylsiloxanes, guerbet esters, and combinations thereof.

TEST METHODS

Silicon Analysis

The amount of elemental silicon coated on the nonwoven structures was determined by silicon analysis performed at an external accredited laboratory using compendial methods.

Liquid Strike Through

The barrier performance of the coated substrates is determined by measuring the time in which a liquid added to the surface of the substrate penetrates the surface of the substrate. The test method conforms to the EDANA method 150.3-96 using a Lister SN L5725 Model 1998 and an aqueous solution of 0.042% Triton-X-100, which is commercially available through Aldrich Chemicals. The surface surface tension of the solution should be approximately 30 mN/m-32 mN/m). The test solution is prepared by the following procedure:

Materials Needed:
  2.6 g Triton-X-100
  1.0 L Beaker
  6.0 L Erlenmeyer Flask
  1.0 L Graduated Cylinder
  Stir Bar
  Distilled Water
  Analytical Balance (at least 1 kg capacity/2-place)
  Foil Procedure to Prepare 5.0 L:
  1. Thoroughly clean and rinse a 6.0 L flask and 1.0 L beaker.
  2. Zero the Analytical Balance with doors/lid closed.
  3. Place the clean, dry 1.0 L beaker onto the balance, and tare the balance.
  4. Using a disposable pipette, carefully add 2.10 g of Triton-X-100 directly to the beaker that is on the balance. Ensure that as you are adding the Triton-X-100 to the flask, you are not getting it on the neck or sides of the beaker.
  5. Using a 1.0 L graduated cylinder, add 998 mL of distilled water to the beaker.
  6. Pour the contents of the beaker into the 6.0 L flask.
  7. Add 1000 mL of distilled water to the beaker to rinse the Triton-X-100.
  8. Pour the distilled water into the 6.0 L flask, combining the contents.

9. Repeat steps 6.-8. three additional times.
10. Place a stir bar into the flask.
11. Cover the flask with foil.
12. Place a Safety Label onto the flask (see example below). Use a piece of masking tape to denote the date of preparation and the initials of the person who prepared the solution.
13. Place the flask of solution onto a stir plate to thoroughly mix (approximately 30 minutes should be sufficient).
14. Measure the surface tension of the solution to ensure that it is 32±2 dyne/cm.

EXAMPLES

Example 1

A hydrophobic surface coating of the present invention is prepared by spraying, dipping, or employing a kiss-roll process of an aqueous mixture of vinyl terminated polydimethyl siloxane and methylhydrogen polydimethyl siloxane in a 30:1 ratio in order that at least about 400 µg/g of the aqueous silicone mixture is deposited on the substrate. Suitable substrates for use in this example include the light-weight nonwoven laminates having a spunbond/meltblown/spunbond laydown in gsm of 6/1/6. 7/1/7, and 8/1/8. The light-weight nonwoven laminates are commercially available from various suppliers. The aqueous mixture also contains a transition metal catalyst to facilitate the self-crosslinking of the PDMS polymers. The wet coated substrate is dried at 120° C. for 0.5-1.0 minutes and is then stored in a suitable container for later use.

Example 2

A nonwoven diaper cuff component treated with a hydrophobic surface coating is prepared. A 3% solution of a vinyl terminated PDMS (commercially available from GE Silicones as SM3200) and a methyl hydrogen PDMS (commercially available from GE Silicones as SM3010) is prepared and mixed for 30 minutes. A typical leg cuff material, such as the light-weight nonwoven laminates disclosed in Example 1, is dipped into the solution and the excess liquid squeezed out in order that approximately at least about 400 µg/g of the aqueous silicone mixture is deposited on the nonwoven laminate. The cuff material is dried as described in Example 1 and is incorporated into a diaper constructing in a similar manner to the diaper detailed in U.S. Pat. No. 6,420,627. (Particularly, the cuff design of the present example is substantially similar to the cuff design in FIG. 3 of U.S. Pat. No. 6,420,627. The meltblown nonwoven web (92) of U.S. Pat. No. 6,420,627 is substituted with the hydrophobic surface coated light-weight nonwoven laminate described in this example.)

Example 3

A nonwoven diaper cuff and/or outer cover component treated with a hydrophobic surface coating is prepared. A 3% solution of a hydroxyl terminated PDMS (commercially available from GE Silicones as SM2245) and a methyl hydrogen PDMS (commercially available from GE Silicones as SM2014c) is prepared and mixed for 30 minutes. A typical leg cuff and/or outer cover material, such as the light-weight nonwoven laminates disclosed in Example 1, is dipped into the solution and the excess liquid squeezed out in order that approximately at least about 400 µg/g of the aqueous silicone mixture is deposited on the nonwoven laminate. The cuff and/or backsheet components are dried at 120° C. for 0.5-1.0 minutes and incorporated into a diaper constructing in a similar manner to the diaper detailed in U.S. Pat. No. 6,420,627. (Particularly, the cuff design of the present example is substantially similar to the cuff design in FIG. 3 of U.S. Pat. No. 6,420,627. The meltblown nonwoven web (92) of U.S. Pat. No. 6,420,627 forms a barrier cuff and may be substituted with the hydrophobic surface coated light-weight nonwoven laminate described in this example. Likewise, the nonwoven web (90) of U.S. Pat. No. 6,420,627 forms an outer cover and may be substituted with the hydrophobic surface coated light-weight nonwoven laminate described in this example.)

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. An absorbent article comprising:
   a) a liquid pervious first topsheet having an interior surface and an exterior surface;
   b) a backsheet having an interior surface and an exterior surface wherein said backsheet is at least partially joined to said topsheet;
   c) an absorbent core disposed between said topsheet and said backsheet;
   d) a barrier member selected from the group consisting of a core cover, an outer cover, a gasketing cuff, a barrier cuff, an elasticized topsheet, and combinations thereof; wherein said barrier member has an interior and an exterior surface;
      wherein said barrier member comprises a nonwoven laminate, said nonwoven laminate comprising:
      i) a first continuous filaments layer,
      ii) a second continuous filaments layer,
      iii) a fine fiber layer having a basis weight of less than about 1.5 gsm and being disposed between the first continuous filaments layer and the second continuous filaments layer; and
   e) a hydrophobic surface coating disposed on at least one surface of said nonwoven laminate such that the hydrophobic surface coating forms a film on at least a portion of the coated surface, wherein said coating comprises one or more silicone polymers and wherein said coating is free of aminosilicones.

2. The article of claim 1 wherein said silicone polymer is selected from the group consisting of silicone MQ resins, polydimethysiloxanes, crosslinked silicones, epoxy silicones, amido silicones, silicone liquid elastomers, and combinations thereof.

3. The article of claim 2 wherein said silicone polymer is a polydimethylsiloxane selected from the group consisting of vinyl-terminated polydimethsiloxanes, methyl hydrogen dimethylsiloxanes, organo-modified polydimethylsiloxanes, hydroxyl-terminated polydimethylsiloxanes, and combinations thereof.

4. The article of claim 1 wherein silicone polymer possesses a molecular weight of at least about 4000 MW.

5. The article of claim 1 wherein said coating is disposed on said interior surface of said barrier member.

6. The article of claim 1 wherein said coating is disposed on at least one surface of the barrier member in an amount of at least about 400 μg/g.

7. The article of claim 1 wherein said coating increases the average barrier strike through time of the barrier member by at least 1 second using an aqueous 0.04% or less Triton-X-100 solution.

8. The article of claim 1 wherein the barrier member comprising the nonwoven laminate onto which said coating is disposed is substantially free of polymers containing melt additives selected from the group consisting of polydimethylsiloxanes, guerbet esters, and combinations thereof.

9. The article of claim 1 wherein said fine fiber layer has a basis weight of less than about 1.4 gsm.

10. The article of claim 1 wherein said fine fiber layer has a basis weight of less than about 1.2 gsm.

11. The article of claim 1 wherein said fine fiber layer has a basis weight of less than about 1.0 gsm.

12. An absorbent article comprising:
   a) a liquid pervious first topsheet having an interior surface and an exterior surface;
   b) a backsheet having an interior surface and an exterior surface wherein said backsheet is at least partially joined to said topsheet;
   c) an absorbent core disposed between said topsheet and said backsheet;
   d) at least one cuff disposed along an outer edge of the article, said cuff having interior and exterior surfaces; wherein said cuff comprises a nonwoven laminate, said nonwoven laminate comprising:
      i) a first continuous filaments layer,
      ii) a second continuous filaments layer,
      iii) a fine fiber layer having a basis weight of less than about 1.5 gsm and being disposed between the first continuous filaments layer and the second continuous filaments layer; and
   e) a hydrophobic surface coating disposed on at least one surface of said nonwoven laminate such that the hydrophobic surface coating forms a film on at least a portion of the coated surface, wherein said coating comprises one or more silicone polymers and wherein said coating is free of aminosilicones.

13. The article of claim 12 wherein said fine fiber layer has a basis weight of less than about 1.0 gsm.

14. The article of claim 12 wherein the cuff is a barrier cuff comprising a single layer of said nonwoven laminate.

15. The article of claim 12 wherein the cuff is a barrier cuff comprising a multiple layer of said nonwoven laminate.

16. The article of claim 12 wherein the cuff is a dual barrier cuff comprising:
   a) a first barrier cuff, and
   b) a second barrier cuff, wherein said second barrier cuff is positioned nearer to a side edge of the article than said first barrier cuff,
   wherein first barrier cuff and second barrier cuff both comprise said nonwoven laminate.

17. The article of claim 16 wherein the said nonwoven laminate is continuous.

18. A disposable substrate article comprising:
   a) a nonwoven substrate; said nonwoven substrate comprising:
      i) a first continuous filaments layer,
      ii) a second continuous filaments layer,
      iii) a fine fiber layer having a basis weight of less than about 1.5 gsm and being disposed between the first continuous filaments layer and the second continuous filaments layer; and
   b) a hydrophobic surface coating disposed on at least one surface of said substrate such that the hydrophobic surface coating forms a film on at least a portion of the substrate, wherein said coating comprises one or more silicone polymers and wherein said coating is free of aminosilicones.

19. The article of claim 18 wherein said article is selected from the group consisting of disposable garments, wiping cloths, cleaning cloths, shoe covers, packing materials, drapes, and combinations thereof.

20. The article of claim 18 wherein said fine fiber layer has a basis weight of less than about 1.0 gsm.

* * * * *